US006641542B2

(12) United States Patent
Cho et al.

(10) Patent No.: US 6,641,542 B2
(45) Date of Patent: Nov. 4, 2003

(54) METHOD AND APPARATUS TO DETECT AND TREAT SLEEP RESPIRATORY EVENTS

(75) Inventors: Yong Kyun Cho, Maple Grove, MN (US); Luc R. Mongeon, Minneapolis, MN (US); Mark K. Erickson, Brooklyn Park, MN (US); H. Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/133,009

(22) Filed: Apr. 26, 2002

(65) Prior Publication Data

US 2002/0193697 A1 Dec. 19, 2002

Related U.S. Application Data

(60) Provisional application No. 60/287,650, filed on Apr. 30, 2001.

(51) Int. Cl.[7] .............................. A61B 5/08; A61B 5/05
(52) U.S. Cl. .................. 600/529; 600/547; 600/536
(58) Field of Search .................................. 600/532, 529, 600/534, 536, 533, 547

(56) References Cited

U.S. PATENT DOCUMENTS

| 5,335,657 | A | | 8/1994 | Terry et al. |
| 5,540,731 | A | | 7/1996 | Testerman ............... 607/42 |
| 5,540,733 | A | | 7/1996 | Testerman et al. |
| 5,591,216 | A | | 1/1997 | Testerman et al. ....... 607/42 |
| 5,765,563 | A | | 6/1998 | Vander Schaaf et al. |
| 5,876,353 | A | * | 3/1999 | Riff ......................... 600/547 |
| 5,958,902 | A | | 9/1999 | Meyer et al. |
| 6,064,910 | A | | 5/2000 | Andersson et al. ........ 607/20 |
| 6,091,973 | A | | 7/2000 | Colla et al. |
| 6,126,611 | A | | 10/2000 | Bourgeois et al. ........ 600/529 |
| 6,480,733 | B1 | * | 11/2002 | Turcott ..................... 600/516 |

FOREIGN PATENT DOCUMENTS

| EP | 0 940 155 A2 | 8/1999 | |
| EP | 0 970 713 | 1/2000 | .......... A61M/16/00 |
| EP | 0 940 155 A3 | 8/2000 | |
| WO | WO 99/61088 | 12/1999 | |
| WO | WO 00/01438 | 1/2000 | .......... A61M/16/00 |

OTHER PUBLICATIONS

Garrigue et al., "Benefit of Atrial Pacing in Sleep Apnea Syndrome", *N Eng J Med,* vol. 346, No. 6, pp. 404–412, Feb., 7, 2002.

Garrique et al., "Night Atrial Overdrive with DDD Pacing: A New Therapy for Sleep Apnea Syndrome", *PACE,* Apr. 2000, vol. 23, No. 4, part 2, p. 700.

* cited by examiner

*Primary Examiner*—Max F. Hindenburg
*Assistant Examiner*—Navin Natnithithadha
(74) *Attorney, Agent, or Firm*—Girma Wolde-Michael; Michael C. Soldner (57) ABSTRACT

The present invention provides a method and apparatus for detecting and treating sleep respiratory events that includes a plurality of sensors gathering physiological data related to sleep respiratory events. A processor extracts an average cycle length and a frequency of at least one of Cheyne-Stokes respiration and periodic breathing based upon the physiological data, and determines whether therapy is required based on the average cycle length and the frequency.

12 Claims, 6 Drawing Sheets

METHOD AND APPARATUS TO DETECT AND TREAT SLEEP RESPIRATORY EVENTS

RELATED APPLICATIONS

This application claims priority from U.S. Provisional Patent Application Ser. No. 60/287,650, filed Apr. 30, 2001, entitled "IMPROVED SYSTEM AND METHOD FOR TREATING SLEEP APNEAS", incorporated herein by reference in its entirety.

BACKGROUND OF THE INVENTION

This invention relates generally to implantable medical devices, and more particularly, to a method and apparatus for detecting and treating sleep apnea.

DESCRIPTION OF THE RELATED ART

Although the function of sleep is not well understood, one obvious consequence of an inadequate quantity or poor quality of sleep is an inability to maintain adequate wakefulness. However, while there are many medical conditions that can prevent a person from receiving a good night's rest, one such condition is sleep apnea.

Sleep apnea is generally defined as the cessation of breathing during sleep, and usually comes in at least one of two basic types. The more common type of sleep apnea is obstructive sleep apnea ("OSA"), which is generally characterized by repetitive pauses in breathing during sleep due to the obstruction and/or collapse of the upper airway, usually accompanied by a reduction in blood oxygen saturation.

The less common type of sleep apnea, central sleep apnea (CSA), is generally defined as a neurological condition causing cessation of substantially all respiratory effort during sleep, usually accompanied with decreases in blood oxygen saturation. In other words, the airway is not necessarily blocked, but the brain fails to send the appropriate signals to the breathing muscles to initiate respirations. As a result, respiratory effort ceases during periods of CSA. Additionally, a patient with CSA is generally aroused from sleep by an automatic reflex to breathe. Such arousal may prevent the patient from receiving a deep, restful sleep.

One common form of central sleep apnea, commonly known as Cheyne-Stokes respiration (CSR), is generally a breathing pattern that is first shallow and infrequent and then increases gradually to become abnormally deep and rapid, before fading away completely for a brief period. Breathing may be stopped for an extended time period, before the next cycle of shallow breathing begins. CSR is common in patients with CHF. It should be noted that some patients have some combination of OSA and CSA, which is commonly known as mixed sleep apnea.

Sleep apnea may cause a variety of medical and other problems among patients. Cycles of sleep, snoring, obstruction, arousal, and sleep may occur many times throughout the night. Although such nocturnal arousals may last only a few seconds, they prevent a person from reaching the deep sleep stages (i.e., stage 3–4 and rapid eye movement (REM) sleep), which the body generally needs to rest and replenish its strength.

Furthermore, multiple arousals with sleep fragmentation are likely to cause excessive daytime sleepiness and fatigue, cognitive impairment, depression, headaches, chest pain, and diminished sexual drive. Sleep apnea is generally associated with cardiovascular morbidity, including systemic hypertension, pulmonary hypertension, ischemic heart disease, stroke, and cardiac arrhythmias. Sleep apnea is also usually associated with increased mortality by negatively affecting the status, progression, and outcomes of previously existing conditions, such as congestive heart failure ("CHF").

OSA is a disorder that is generally underdiagnosed and undertreated. Because OSA may worsen the effects of a previously existing condition, such as CHF, treatment of OSA may be beneficial to reduce its negative on the previously existing condition. Once OSA has been properly diagnosed, a variety of therapies may be available. Common OSA therapies include non-surgical methods, such as continuous positive airway pressure ("CPAP"), as well as surgical methods, such as uvulopalatopharyngoplasty ("UPPP"). Effective therapy for OSA can often reverse or ameliorate the problems associated with OSA.

One method of diagnosis for sleep apnea is polysomnography. In polysomnography, multiple physiological parameters are measured while the patient sleeps in a sleep laboratory. Typical parameters in a polysomnography include eye movement observations (to determine whether a patient has reached REM sleep), an electroencephalogram (to determine arousals from sleep), chest wall monitors (to document respiratory movements), nasal and oral air flow measurements, and an electrocardiogram, among other parameters. A combination of these and other factors are used by doctors and other qualified sleep specialists to determine whether a patient has sleep apnea. However, an overnight sleep study is generally expensive and time-consuming. As a result, many patients with sleep apnea may not seek proper diagnosis or treatment of their sleeping disorder from a doctor or other qualified sleep specialist. Even if a patient is diagnosed with sleep apnea, frequent laboratory monitoring of the patient is generally not feasible due to the expense and time involved in a nocturnal polysomnography.

The technology explosion in the implantable medical devices industry has resulted in many new and innovative devices and methods for analyzing and improving the health of a patient. The class of implantable medical devices now includes pacemakers, implantable cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well proven.

There are many implementations of implantable medical devices that provide data acquisition of important physiological data from a human body. Many implantable medical devices are used for cardiac monitoring and therapy. Often these devices include sensors that are placed in blood vessels and/or chambers of the heart, and are operatively coupled with implantable monitors and therapy delivery devices. For example, such cardiac systems include implantable heart monitors and therapy delivery devices, such as pacemakers, cardioverters, defibrillators, heart pumps, cardiomyostimulators, ischemia treatment devices, drug delivery devices, and other heart therapy devices. Most of these cardiac systems include electrodes for sensing and gain amplifiers for recording and/or driving sense event signals from the inter-cardiac or remote electrogram ("EGM").

Many patients who use implantable medical devices may be at risk for sleep apnea. However, patients are generally left with traditional forms of diagnosis for sleep apnea, such as polysomnography. As mentioned, polysomnography may be an expensive and time-consuming procedure. Furthermore, many patients may not recognize that they have symptoms relating to sleep apnea, such that they would seek diagnosis and treatment for the disorder. Polysomnography is generally an infrequent procedure that does not provide long term monitoring of the patient's condition after the patient has been diagnosed. Even after a patient is diagnosed with sleep apnea, traditional methods of treatment such as CPAP may be time-consuming and costly.

SUMMARY OF THE INVENTION

In one aspect of the present invention, a method is provided for detecting and treating sleep apnea. The method includes gathering information from an implantable sensor device for detecting sleep apnea, extracting an average cycle length and a frequency of at least one of Cheyne-Stokes respiration and periodic breathing based upon the information gathered from the implantable sensor device, performing diagnostics and decision on the average cycle length and the frequency to form results, and delivering therapy in response to the results of the diagnostics for treating sleep apnea.

In another aspect of the present invention, an apparatus is provided for detecting and treating sleep apnea. The apparatus includes an implantable first sensor adapted to gather information related to sleep apnea, a program for extracting an average cycle length and a frequency of at least one of Cheyne-Stokes respiration and periodic breathing based upon the information gathered, a program for performing diagnostics and decision on the average cycle length and the frequency to form results, an implantable second sensor adapted to deliver therapy in response to the results of the diagnostics, a data acquisition controller adapted to receive data from at least one of the first sensor and the second sensor, a control logic adapted to control the medical device, and a processor adapted to utilize the control logic to provide data from the data acquisition controller to a memory unit.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving the operation of implantable medical devices (e.g., pacemakers, implantable cardiovertor defibrillators, the like). The operation of an implantable medical device includes collecting, storing, and analyzing physiological data relating to a patient, and/or delivering therapy (e.g., cardiac therapy) to a portion of a patient's body. Often, these tasks are performed by an implantable medical system, which includes an implantable medical device. Based upon the analysis performed by the implantable medical system, one or more therapies may be delivered to a particular portion of a patient's body. One example of such a therapy is a cardiac pacing therapy, which is delivered to a patient's heart.

Embodiments of the present invention may be utilized to detect the common symptoms and conditions related to patients with the various forms of sleep apnea and to provide an appropriate treatment. It should be appreciated that the present invention may be included in an implantable device capable of collecting data other than data used to diagnose and treat sleep apnea. The data may be collected by sensors in the implantable device and may be used by doctors and other sleep experts to judge the severity of apneas and to determine the most applicable apnea therapy, without the use of polysomnography.

Figure 1:
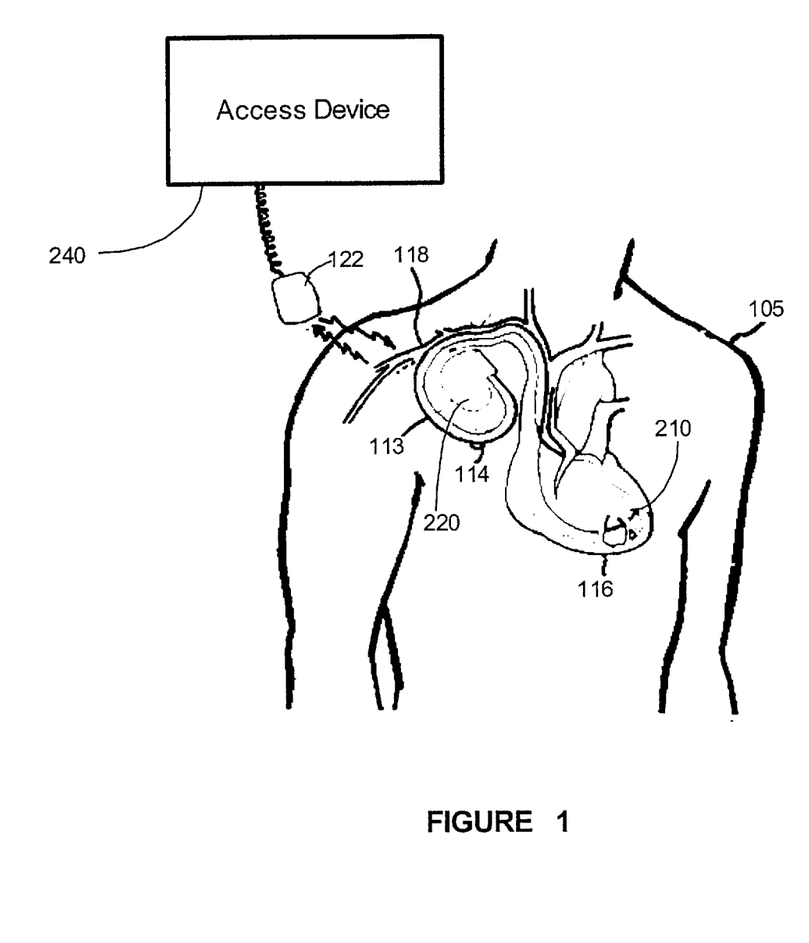
FIG. 1 is a simplified diagram of an implementation of an implantable medical device, in accordance with one illustrative embodiment of the present invention.

Turning now to FIG. 1, one embodiment of implementing an implantable medical device into a human body is illustrated. A sensor device 210 (e.g., devices attached to leads 114) placed upon the heart 116 of the human body 105 is used to acquire and process physiological data. In one embodiment, the sensor device 210 may also be a therapy delivery device (described in greater detail below). An implantable medical device 220 collects and processes a plurality of data acquired from the human body 105. In one embodiment, the implantable medical device 220 may be a cardiac pacemaker or an implantable cardiovertor defibrillator ("ICD"). The data acquired by the implantable medical device 220 can be monitored by an external system, such as the access device 240 including a programming head 122, which remotely communicates with the implantable medical device 220. The programming head 122 is utilized in accordance with medical device programming systems known to those skilled in the art having the benefit of the present disclosure, for facilitating two-way communication between the implantable medical device 220 and the access device 240.

In one embodiment, a plurality of access devices 240 can be employed to collect a plurality of data, including sleep data, processed by the implantable medical device 220 in accordance with embodiments of the present invention. The implantable medical device 220 is housed within a hermetically sealed, biologically inert outer canister or housing 113, which may itself be conductive so as to serve as an electrode in the implantable medical device 220 pacing/sensing circuit. One or more sensors/leads, collectively identified with reference numeral 114 in FIG. 1, are electrically coupled to the implantable medical device 220 and extended into the patient's heart 116 via a vein 118. Disposed generally near a distal end of the leads 114 are one or more exposed conductive electrodes (i.e., sensor device 210) for receiving electrical cardiac signals or delivering electrical pacing stimuli to the heart 116. The leads 114 may be implanted with their distal end situated in either the atrium or ventricle of the heart 116. In an alternative embodiment, the sensor device 210, or the leads 114 associated with the sensor device 210, may be situated in a blood vessel on the heart 116, such as a vein 118.

Figure 2:
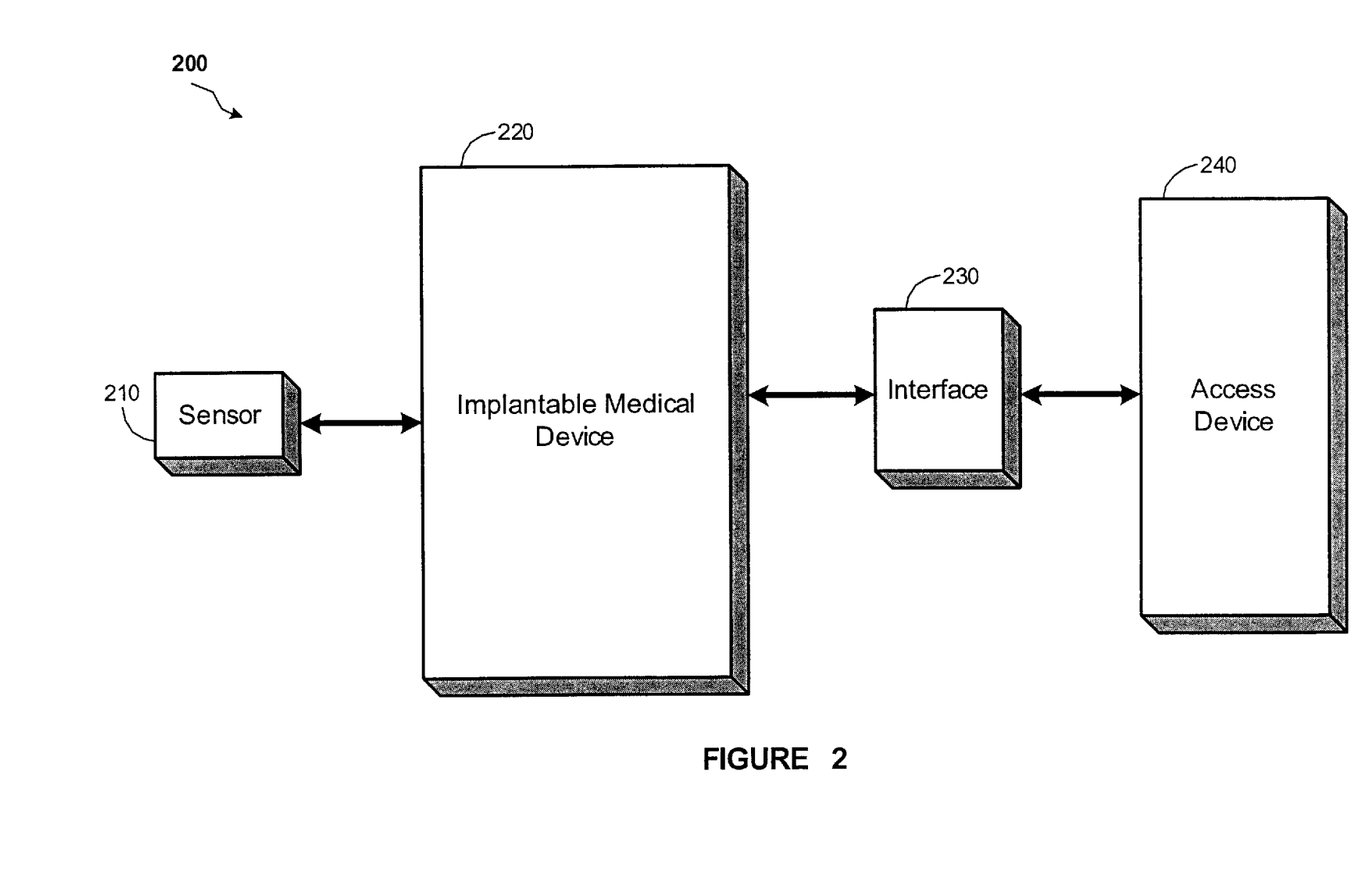
FIG. 2 is a simplified block diagram representation of an implantable medical system in accordance with one illustrative embodiment of the present invention.

Turning now to FIG. 2, a system 200, in accordance with one embodiment of the present invention, is illustrated. The system 200 comprises a sensor device 210, an implantable medical device 220, an access device 240, and an interface 230 that provides a communication link between the implantable medical device 220 and the access device 240. As described in greater detail below, the sensor device 210 may comprise at least one of a variety of sensors that aid in the detection of sleep apnea. For the sake of simplicity, only one sensor device 210 is illustrated. Embodiments of the present invention provide a plurality of physiological data from the sensor device 210, which are then processed and stored in the implantable medical device 220. In one embodiment, the sensor devices 210 may collect data that is used to detect and treat sleep apnea in a patient.

As mentioned, based upon physiological data and other factors, the implantable medical device 220 may deliver a therapy to a portion of the patient's body, via the sensor device 210. It should be appreciated that other embodiments of the present invention may deliver therapy to a patient via a device other than the sensor device 210. The access device 240 can then be used to monitor and analyze the organized data from the implantable medical device 220 via the interface 230 and view results from delivered therapy. The access device 240 can be used to monitor the efficiency of the therapy delivered by the implantable medical device 220. The access device 240 can be used to determine, based upon data stored by the implantable medical device 220, whether a therapy delivered was of proper energy intensity.

Figure 3:
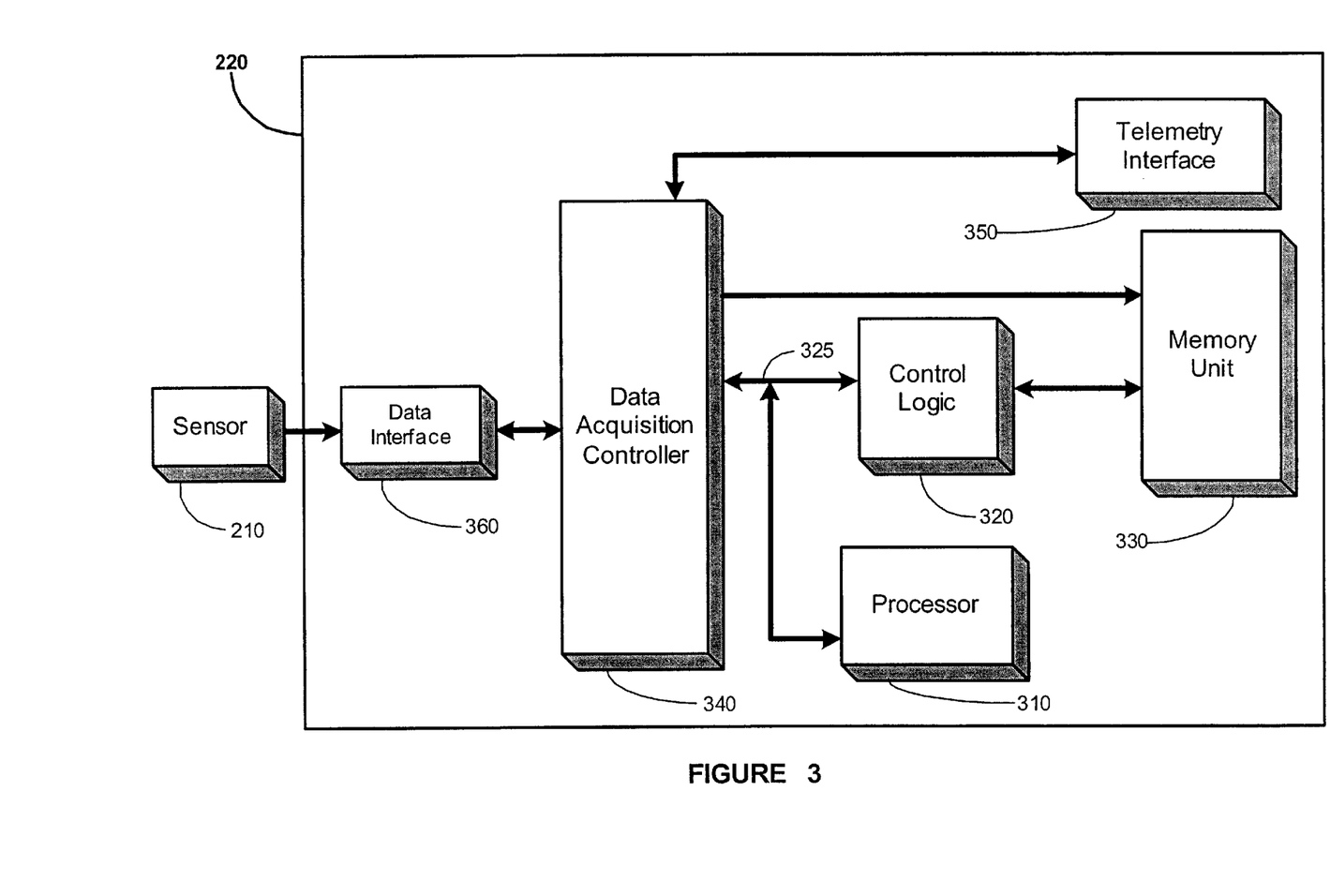
FIG. 3 is a more detailed block diagram representation of the implantable medical system of FIGS. 1 and 2, in accordance with one illustrative embodiment of the present invention.

Turning now to FIG. 3, a more detailed block diagram depiction of one embodiment of the implantable medical device 220 is illustrated. The implantable medical device 220 includes a processor 310, a control logic 320, a memory unit 330, a data acquisition controller 340, a telemetry interface 350, and a data interface 360. The sensor device 210 provides various physiological data to the implantable medical device 220. As mentioned, only one sensor device 210 is illustrated. However, the sensor device 210 may comprise at least one of a variety of sensors in accordance with conventional practice for the detection of sleep apnea. Similarly, only one data interface 360 is illustrated for the sake of simplicity. However, more than one data interface 360 may be used in accordance with conventional practice. The processor 310 controls the operation of the implantable medical device 220. The processor 310 utilizes the control logic 320 to perform a plurality of operations, including memory access and storage operations. The processor 310 communicates with the control logic 320 and the data acquisition controller 340 via a bus line 325. The control logic 320 sends control signals to the memory unit 330 for controlling and installing the memory unit 330, and to the data acquisition controller 340, which controls the acquisition of physiological data and drives output signals to the telemetry interface 350. The memory 330 may comprise at least one of a variety of programs, including programs for parameter extraction and programs for diagnostics and decision, as described in greater detail below.

The telemetry interface 350 can facilitate real-time access of physiological data acquired by the data acquisition controller 340. Therefore, a physician can view physiological data on a real time basis by accessing the data acquisition controller 340, via the telemetry interface 350. The data acquisition controller 340 can prompt the data interface 360 to retrieve physiological data from the sensor device 210, process such data, and deliver physiological data to the data acquisition controller 340. The data interface 360 can perform a number of analog-to-digital conversions and time-interval conversions, known to those skilled in the art, upon the acquired physiological data. The data interface 360 can acquire, condition, and process physiological data and forward them to the data acquisition controller 340.

It should be appreciated that, in an alternate embodiment, the functionality of the data interface 360 may be combined with the sensor device 210, such that information gathered by the sensor device 210 may be readily utilized by the implantable medical device 220 without further processing by another device or interface. It should also be appreciated that, although the sensor devices 210 are separated from the implantable medical device 220 for illustrative purposes in FIGS. 2 and 3, the implantable medical device 220 may further include the sensor devices 210.

Figure 4:
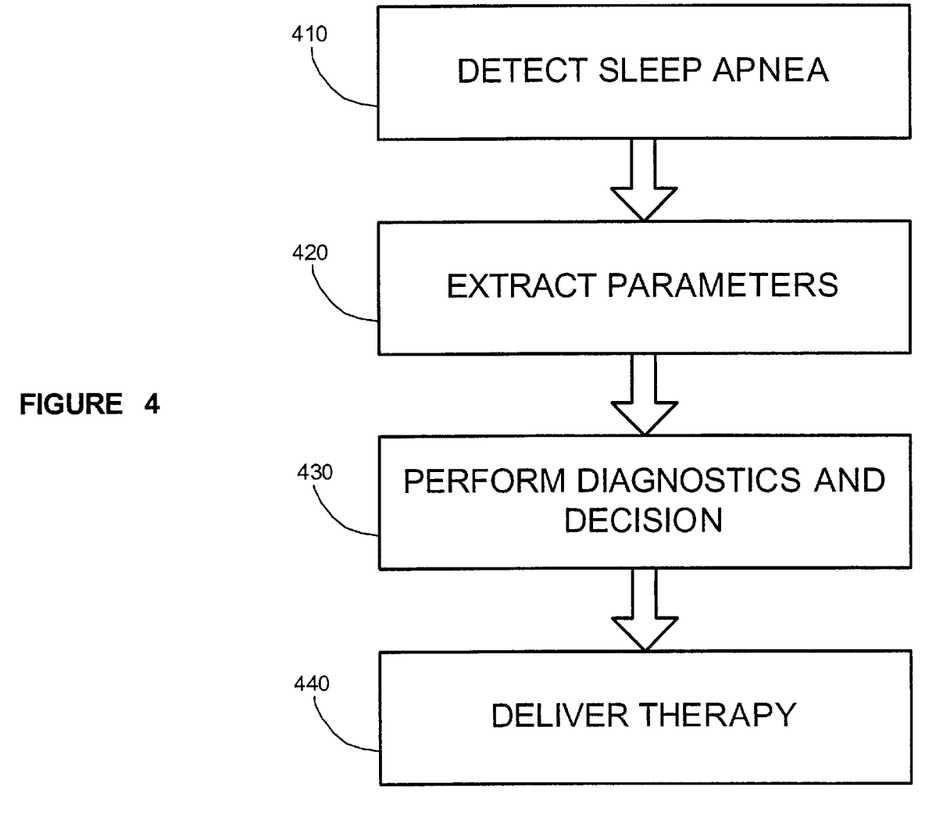
FIG. 4 is a flow diagram of an exemplary method of implementing the implantable medical system of FIGS. 1, 2, and 3, in accordance with one illustrative embodiment of the present invention

Turning now to FIG. 4, a method of implementing the present invention, in accordance with one embodiment, is illustrated. The sensor device 210 of the implantable medical device 220 of FIG. 1 detects (at 410) whether a patient has sleep apnea. In order to detect sleep apnea in a patient, the implantable medical device 220 may incorporate various sensor technologies. It should be appreciated that the sensor device 210 may comprise one or more of the various sensor technologies, as described in greater detail below. Furthermore, it should be appreciated that the sensor device 210 may further be capable of delivering therapy to the patient and providing patient monitoring data.

Figure 5:
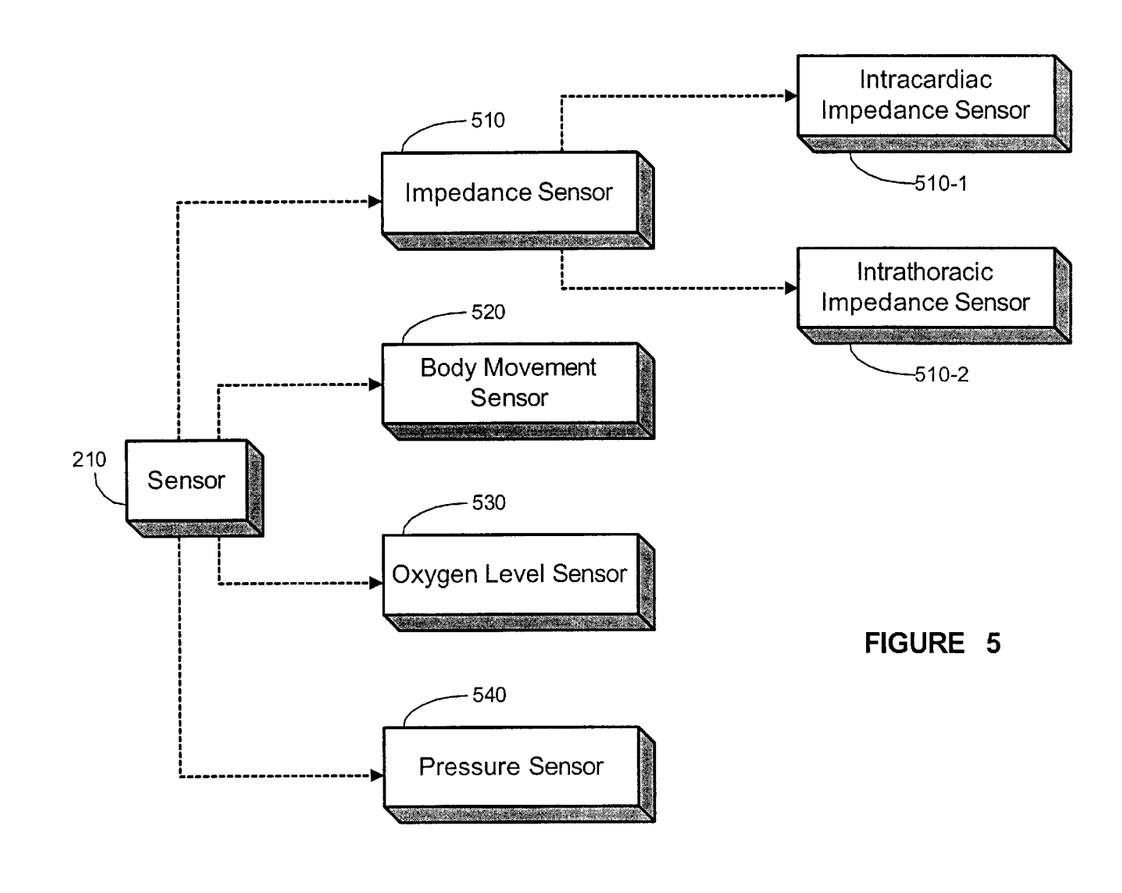
FIG. 5 is a graphical diagram of a plurality of various sensors that may be implemented in the implantable medical system of FIGS. 1, 2, and 3, in accordance with one illustrative embodiment of the present invention.

Turning now to FIG. 5, the sensor device 210 may comprise at least one of the following: an impedance sensor 510, a body movement sensor 520, an oxygen level sensor 530, and a blood pressure sensor 540. It should be appreciated that the present discussion of various sensor technologies is not exhaustive. However, it is noted that the sensor device 210 generally measures at least one of a variety of indices relating to sleep apnea. The indices are typically referred as adverse events. Adverse events are the measurable events indicating abnormal sleep. Adverse events may include apnea, hypopnea (regardless the origin, type, arousals, limb movements, etc.), Cheyne-Stokes respiration ("CSR"), periodic breathing, and abnormal arousals, among other events.

The sensor device 210 may comprise various other sensors, in accordance with conventional practice. In one embodiment, the sensor device 210 may be an impedance sensor 510. The impedance sensor 510 may measure, among other things, respiration and cardiac condition. In one example, the impedance sensor 510 may be an intracardiac impedance sensor 510-1, which measures impedance between an intracardiac atrial electrode and an intracardiac ventricular electrode. A large decrease in impedance between atrial and ventricular electrodes (i.e., a decrease in the intracardiac impedance) may be an indication of sleep apnea. As a patient attempts to breath while his airway is obstructed, intrathoracic pressure may decrease, which overfills the right side of the heart. This overfilling of the right side of the heart increases the diameter of the atrium and the ventricle. Although the volume of the heart does not change, the shape of the heart becomes shorter and wider. As a result, a drop in atrial-to-ventricular impedance may be observed during sleep apnea because the wider blood pool will cause a reduced impedance.

In another example, the impedance sensor 510 may be an intrathoracic impedance sensor 510-2, which measures impedance across the thorax. A decrease in intrathoracic impedance during attempted respiration may be a factor in determining whether a patient has sleep apnea. As a patient attempts to breathe while his airway is obstructed, the circumference of his thorax may expand. As the patient's thorax expands, the diaphragm pushes the heart and lungs upward. As the lungs are pushed upward, the lungs do not change volume, but instead become shorter and wider. The shorter and wider shape of the lungs may reduce intrathoracic impedance. In addition, upward movement of the diaphragm pushes the heart closer to the implantable medical device 220, thereby reducing impedance.

Another possible indication that a patient has sleep apnea comes from a rapid increase in impedance minute ventilation ("MV") followed by a slower decrease in impedance MV. In one embodiment, the impedance sensor 510 may include pacemaker sensors (not shown) that measure impedance between a pacemaker and an intracardiac electrode. The impedance between the pacemaker and the intracardiac electrode may be used to estimate in MV. During an arousal from sleep apnea, the patient goes through a hyperpneic phase, which is a period of abnormally rapid or deep breathing ("hyperventilation"). Studies have shown that during the hyperpneic phase there may be an immediate rise in MV. However, as the patient goes through an apneic phase, MV gradually decreases.

The sensor device 210 may be a body movement sensor 520. Embodiments of the body movement sensor 520 may comprise a piezo crystal or an accelerometer. The body movement sensor 520 may be used alone. For example, during the hyperpneic phase following the release of an obstruction, there is usually a brief arousal, which can cause body movement detectable by movement sensors. The body movement sensor 520 may also be used in conjunction with one or more other sensors. For example, it is described above that a reduction of intracardiac impedance by the impedance sensor 510 may be caused by a wider blood pool. However, the wider blood pool may also be a result vigorous exercise from the patient. Therefore, the impedance sensor 510 may be read in conjunction with the body movement sensor. In one embodiment, a low reading from the body movement sensor 520 indicates the patient is not physically active. Accordingly, a decrease in the impedance sensor 510 and a low reading from the body movement sensor 520 may indicate the patient has sleep apnea. Furthermore, a brief period of movement during sleep coinciding with the dramatic increase in respiration (i.e., a rapid increase in impedance MV followed by a slower decrease in impedance MV) may indicate the patient has sleep apnea.

The sensor device 210 may be an oxygen sensor 530, which measures oxygen saturation level in blood and tissue. Sleep apnea generally causes a drop in one's blood oxygen saturation ("$SaO_2$") and an increase in the blood's carbon dioxide ("$CO_2$"). When the $SaO_2$ drops, the heart may start pumping more blood with each beat. As the $CO_2$ increases, the brain may try to drive the person to breathe. The effort and action of the abdomen and chest may increase. Eventually, the increased $CO_2$ level causes an arousal, thereby resuming respiration. This sequence of events may occur a plurality of times throughout a night for a patient with sleep apnea. The oxygen sensor 230 may measure at least one of the oxygen saturation level of the blood and tissue and the carbon dioxide level of the blood and tissue. As mentioned, a decrease in blood saturation and/or an increase in carbon dioxide may indicate the patient has sleep apnea.

The sensor device 210 may also be a pressure sensor 540. In one embodiment, the pressure sensor 540 may be mounted on a lead 114 to measure intracardiac blood pressure. Intracardiac blood pressure may include either absolute pressure or relative pressure, generally depending on the ability of the pressure sensor 540 to calibrate automatically. Studies have shown that the risk of hypertension (i.e., high blood pressure) may increase with the severity of sleep apnea in a patient. Detecting hypertension is important because it is a major factor for cardiovascular disease, which may lead to heart failure and ultimately death. Accordingly, the pressure sensor 540 may indicate a risk of sleep apnea in a patient by detecting a sudden change in the pressure. In another embodiment, the pressure sensor 540 may measure any of a variety of surrogates of pressure measurement. The surrogate of pressure measurement may comprise data from other sensors that have a high correlation with pressure values, such as impedance.

It should be appreciated that results of the sensor device 210 are generally stored in the memory unit 330 of FIG. 3, as described above. However, other embodiments are possible. For example, the results of the sensor device 210 may be stored on an external memory source separate from the implantable device 220, and/or the results may be transmitted to a remote location for processing and/or storage.

Referring back to FIG. 4, as the sensor device 210 gathers various data from the patient to detect (at 410) sleep apnea, at least one of a variety of parameters are extracted (at 420). Although not so limited, the extraction (at 420) may be performed in response to processor-based system instructions (i.e., a program) capable of being processed by the processor 310 of FIG. 3. In one embodiment, an Apnea Hypopnea Index ("AHI") (i.e., Respiration Disturbance Index ("RDI")) may be extracted. It is generally the standard in clinical practice and epidemiological studies to assess the severity of sleep-disordered breathing by combining the number of apneas and hypopneas per hour of sleep. The AHI generally refers to the total number of apneas and hypopneas divided by the total sleep time in a patient's sleep study. The AHI gives one measure of the severity of the sleep apnea.

In an alternate embodiment, another parameter that may be extracted includes an average cycle length and frequency of a periodic breathing and/or Cheyne-Stokes respiration ("CSR") during a patient's sleep study. This parameter may be used to monitor the possibility of congestive heart failure ("CHF"). It should be appreciated that the above discussion is not exhaustive, and at least one of a variety of parameters may be extracted (at 420), in accordance with conventional practice. Similarly to the results collected from the sensor devices 210, as described above, the parameters are generally stored in the memory unit 330 of FIG. 3. However, other embodiments are possible. For example, the parameters may be stored on an external memory source separate from the implantable device 220, and/or the results may be transmitted to a remote location for processing and/or storage.

It should also be appreciated that the parameters, as described above, generally refer to occurrences, such as apneas and hypopneas in the case of AHI, over a period of time (i.e., the length of a patient's sleep time). AHI may be measured upon any measure of time, for example, a nightly basis. Furthermore, the AHI for each measure of time may be stored in the memory unit 330 of the implantable medical device 220. The detecting (at 410) of sleep apnea and the extraction (at 420) of parameters over the period of time provides an effective and efficient method to detect and monitor at least one of a plurality of indices relating to a patient's sleep apnea.

Diagnostics are performed (at 430) regarding the severity of sleep apnea and a decision is made whether to deliver therapy to the patient. Although not so limited, the diagnostics (at 430) may be performed in response to processor-based system instructions (i.e., a program) capable of being processed by the processor 310 of FIG. 3. Diagnostics may provide a clinician the opportunity to monitor a patient's sleep apnea, and therefore, allows a physician to better decide whether to delivery therapy to the patient. Similarly, diagnostics may provide the physician more information to determine the appropriate therapy to deliver. It should be appreciated that the results of the diagnostics may be stored on the memory unit 330 of the implantable device 220 in FIG. 3 and/or the results may be delivered to a remote location for analysis. It should also be appreciated that the results of the diagnostics may be used by the physician to monitor the severity of sleep apnea.

In one embodiment, the value of a patient's AHI can be compared to certain criteria to determine the severity of sleep apnea syndrome. According to the American Academy of Sleep Medicine, an AHI less than 5 is normal, an AHI greater than or equal to 5 and less than 15 is mild sleep apnea, an AHI greater than or equal to 15 and less than 30 is moderate sleep apnea, and an AHI greater or equal to 30 is severe sleep apnea. In another embodiment, the frequency and cycle length of CSR may be used to measure the progression of congestive heart failure ("CHF"). It should be appreciated that any of a variety of guidelines may be used to diagnose the severity of sleep apnea, in accordance with conventional practice. It should also be appreciated that any of a variety of diagnoses may be made with regard to sleep apnea and its relative complications (e.g., CHF, high blood pressure, etc.), in accordance with conventional practice.

The decision on whether to administer therapy may be performed (at 430) in at least one of a variety of methods, in accordance with conventional practice. Although not so limited, the decision (at 430) may be performed in response to processor-based system instructions (i.e., a program) capable of being processed by the processor 310 of FIG. 3. In one embodiment, an automatic monitoring algorithm can control the delivery of therapy. In another embodiment, the decision to deliver therapy to a patient may be done manually by a physician. The decision on whether to deliver therapy is generally made in reference to the diagnostics performed (at 430). Similarly, the decision on whether to deliver therapy may also comprise the decision on the type of therapy to use and the quantity of the therapy.

The implantable medical device 220 may deliver (at 440) therapy to a patient diagnosed with sleep apnea. It should be appreciated that therapy may be delivered at various times and at various intervals, in accordance with conventional practice. In one embodiment, the therapy for sleep apnea may include atrial overdrive pacing (hereinafter "overdrive pacing"). The use of overdrive pacing as a treatment for sleep apnea is described in greater detail in Garrigue et al., "Benefit of Atrial Pacing in Sleep Apnea Syndrome," N Eng J Med, Vol. 346, No. 6, pp 404–412 (Feb. 7, 2002). That study shows that overdrive pacing significantly reduces the number of episodes of central and obstructive sleep apnea without reducing the total sleep time.

Overdrive pacing generally includes sending electrical signals to the heart to stimulate the heart to beat at a higher rate than the patient's intrinsic rate. It has been shown that overdrive pacing at a rate 15 beats per minute faster than the mean nocturnal heart rate (i.e., the patient's intrinsic rate) resulted in a significant reduction in the number of apneic episodes. Furthermore, the rate of 15 beats per minute faster than the patient's intrinsic rate will generally reduce the frequency of sleep apnea episodes without causing the patient to wake up. Previous efforts to artificially pace the heart to treat sleep apnea, such as the one described in U.S. Pat. No. 6,126,661 to Bourgeois et al., terminated an apneic event by using an unusually high paced heart rate that caused to person to wake up. As a result, the patient may not have received an adequately restful sleep. The present invention treats sleep apnea without waking up the patient, thereby allowing the patient to receive a more restful sleep.

In an alternate embodiment, the therapy for sleep apnea may include temporary overdrive pacing. In temporary overdrive pacing, overdrive pacing therapy may be delivered at a higher rate than the patient's intrinsic rate, for example, 5 to 30 beats per minute faster, and at a programmed time interval. After delivering pacing therapy at the programmed time interval, the pacing rate will decrease by a decremental interval, for example, 5 beats per minute. The pacing therapy will continue at each programmed time interval and the pacing rate will decrease by the decremental interval until the pacing rate reaches the patient's intrinsic rate.

It should also be appreciated that a plurality of other sleep therapies may be delivered (at 280) to the patient, in accordance with conventional practice. For example, U.S. Pat. No. 5,591,216 to Testerman et al. describes a method of treating sleep apnea by applying electrical stimulation to the patient's hypoglossal nerve. In one embodiment, the implantable device 220 may be implemented to deliver such a therapy and other therapies, as well.

Figure 6:
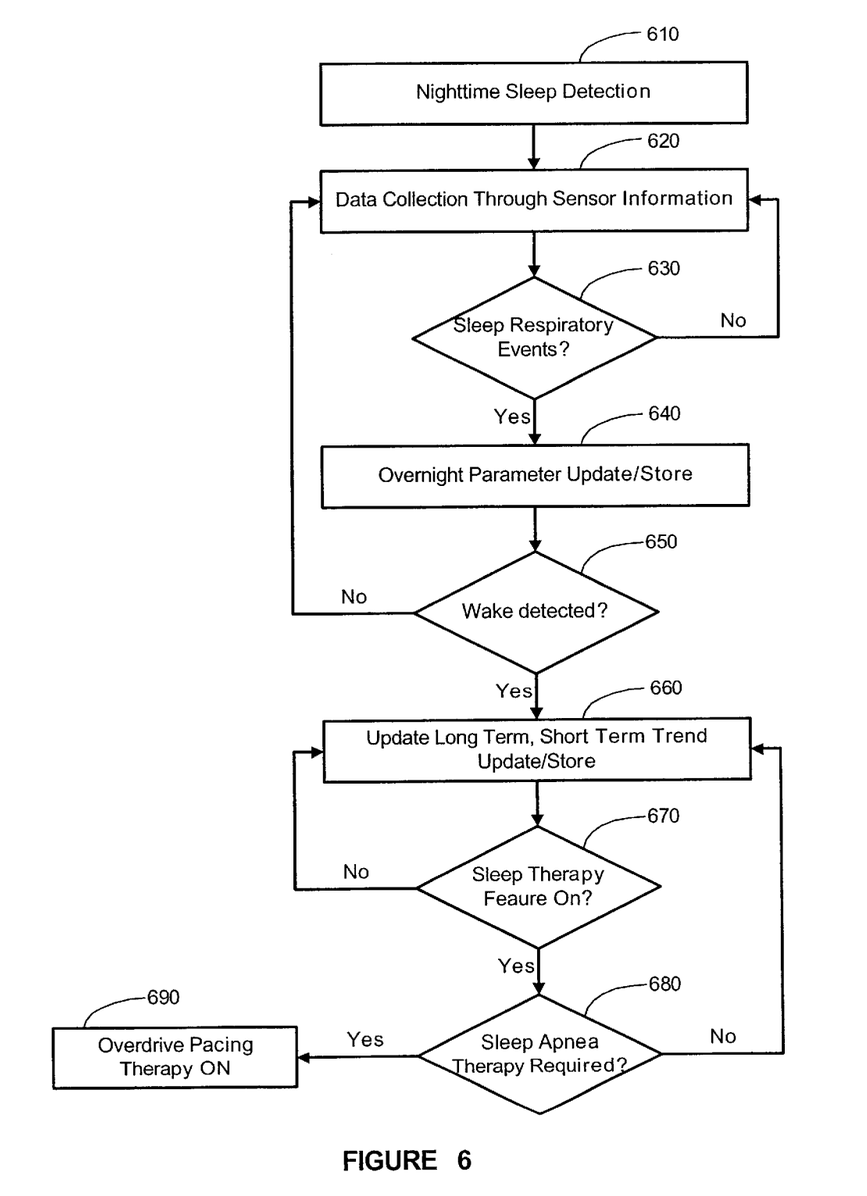
FIG. 6 is a flow diagram of an exemplary method of implementing the implantable medical system of FIGS. 1, 2, and 3, in accordance with one illustrative embodiment of the present invention.

Turning now to FIG. 6, a flowchart depiction of detecting sleep apnea in accordance with one embodiment of the present invention is shown. Once a patient falls asleep, the implantable device 220 begins nighttime sleep detection (at 610). The sensor 210 collects (at 620) various data and stores the information on the memory unit 330 of the implantable device 220, for example. As shown and described in FIG. 5, the sensor device 210 may collect a plurality of information, including, but not limited to, impedance, minute ventilation, body movement, blood oxygen saturation ($SaO_2$), and intracardiac pressure. From the data collected from the sensor device 210, it is determined (at 630) whether any sleep respiratory events have occurred. Examples of sleep respiratory events include apneas and hypopneas. If there are no sleep respiratory events, the sensor device 210 continues to collect (at 620) more data from the patient.

If sleep respiratory events are detected, then each sleep respiratory event is stored (at 640) in the memory unit 330, for example, or it may be used to update (at 640) the information already accrued regarding previous respiratory events throughout the night. For example, each apnea or hypopnea that occurs while the patient is sleeping may cause the value of an apnea hypopnea counter in the memory unit 330 to increment by one. The apnea hypopnea counter generally refers to the total number of apneas and hypopneas divided by the total sleep time in hours in a patient's sleep study.

If it is determined (at 650) the patient is not aroused from sleep (i.e., a wake event) as a result of the sleep respiratory event, the sensor device continues to collect at 620 more data from the patient, and the steps at blocks 620, 630, and 640 may be repeated. If it is determined (at 650) the patient is aroused from sleep (i.e., a wake event) as a result of the sleep respiratory event, the wake event is stored (at 660) in the memory unit 330, for example, or it may be used to update (at 660) the information already accrued regarding previous wake events. Previous wake events may be recorded for a long term or a short term, in accordance with conventional practice.

If it is determined (at 670) that a sleep therapy feature is on and determined (at 680) that sleep therapy is required, then overdrive pacing therapy is turned on (at 690). In one embodiment, the sleep therapy feature may be on when the patient is diagnosed as a good candidate for the therapy being delivered. For example, in the illustrated embodiment, a good candidate for overdrive pacing will have the sleep therapy feature on. In one embodiment, sleep therapy may be required when the AHI for the sleep study reaches above 15 (i.e., moderate or severe sleep apnea). Other embodiments of the present invention may require sleep therapy at a different AHI threshold or as a result of other criteria, in accordance with conventional practice. Once overdrive pacing therapy is on, overdrive pacing therapy is delivered to the patient in accordance with conventional practice. It should be appreciated however that the present invention is not limited to overdrive pacing therapy. Other therapies, such as hypoglossal nerve stimulation, may be used.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A medical device for detecting and treating sleep respiratory events, comprising:
    a plurality of sensors gathering physiological data related to sleep respiratory events; and
    a processor extracting an average cycle length and a frequency of at least one of Cheyne-Stokes respiration and periodic breathing based upon the physiological data, and determining whether therapy is required based on the average cycle length and the frequency.

2. The medical device of claim 1, wherein the plurality of sensors include at least one of an intracardiac impedance sensor, an intrathoracic impedance sensor, a body movement sensor, an oxygen sensor, and a pressure sensor.

3. The medical device of claim 1, wherein the therapy includes overdrive pacing.

4. The medical device of claim 1, wherein the therapy includes hypoglossal nerve stimulation.

5. The medical device of claim 1, further comprising a memory unit storing and updating the sleep respiratory events.

6. The medical device of claim 5, wherein the memory unit stores wake events corresponding to the sleep respiratory events.

7. The medical device of claim 6, wherein the processor determines whether therapy is required based on a predetermined apnea hypopnea index.

8. The medical device of claim 7, wherein the predetermined apnea hypopnea index is 15.

9. A medical device for detecting and treating sleep respiratory events, comprising:
    a plurality of sensors gathering physiological data related to sleep respiratory events;
    a processor extracting an average cycle length and a frequency of at least one of Cheyne-Stokes respiration and periodic breathing based upon the physiological data, and determining whether therapy is required based on the average cycle length and the frequency; and
    a memory unit storing and updating the sleep respiratory events, wherein the plurality of sensors include at least one of an intracardiac impedance sensor, an intrathoracic impedance sensor, a body movement sensor, an oxygen sensor, and a pressure sensor, and wherein the therapy includes one of overdrive pacing and hypoglossal nerve stimulation.

10. The medical device of claim 9, wherein the memory unit stores wake events corresponding to the sleep respiratory events.

11. The medical device of claim 10, wherein the processor determines whether therapy is required based on a predetermined apnea hypopnea index.

12. The medical device of claim 11, wherein the predetermined apnea hypopnea index is 15.

* * * * *